United States Patent [19]
Ayers et al.

[11] Patent Number: 5,814,081
[45] Date of Patent: Sep. 29, 1998

[54] ATRIAL FLUTTER CARDIOVERTER AND METHOD

[75] Inventors: Gregory M. Ayers, Redmond; John M. Adams, Issaquah, both of Wash.

[73] Assignee: InControl, Inc., Redmond, Wash.

[21] Appl. No.: 835,169

[22] Filed: Apr. 7, 1997

[51] Int. Cl.⁶ .................................................. A61N 1/39
[52] U.S. Cl. ..................................................... 607/5
[58] Field of Search ....................................... 607/4, 5, 14

[56] References Cited

U.S. PATENT DOCUMENTS 5,620,468  4/1997  Mongeon et al. ........................... 607/5

OTHER PUBLICATIONS

Keelan et al. "Determination of the Minimum Heart Rate Deleceration for Safe Axriel Defibrillation", *Circulation*, Nov. 1996 Abstracts (405).

Keelan et al. "Atriel Defibrilation Shocks Synchronized to QRS Complexs Preceded by Short to Long Cycles . . . ", Apr. 1996 *Pace* Abstracts (324).

Waldo et al. *"Atrial Flutter"* p. 389.

Keane, "Impact of Pulse Characteristics on Atrial Defibrillation Energy Requirements" *PACE,* May '94 Part II vol. 17, pp. 1048–1056.

*Primary Examiner*—Jeffrey R. Jastrzab
*Attorney, Agent, or Firm*—Richard O. Gray, Jr.

[57] ABSTRACT

An implantable atrial defibrillator includes a lead system having a plurality of electrodes to deliver a cardioverting pulse to atria of a heart, for sensing A waves of the heart, and for sensing R waves of the heart. A first detector detects the A waves sensed by the lead system and a second detector detects the R waves sensed by the lead system. An inhibit stage defines an inhibit time period responsive to each detected R wave and an output provides the cardioverting pulse to the lead system responsive to an A wave being detected. The inhibit stage precludes provision of the cardioverting pulse during each inhibit time period.

12 Claims, 2 Drawing Sheets

ATRIAL FLUTTER CARDIOVERTER AND
METHOD

BACKGROUND OF THE INVENTION

The present invention generally relates to an atrial cardioverter/defibrillator and method for applying cardioverting electrical energy to the atria of a human heart in need of cardioversion. The present invention is more particularly directed to an improved atrial cardioverter which cardioverts atrial flutter or other organized atrial tachyarrhythmia by applying a pulse of cardioverting electrical energy to the atria responsive to detection of an atrial activation and outside an inhibit interval timed from a detected R wave.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience rapid and irregular beating of the heart and may even experience dizziness as a result of reduced cardiac output.

Atrial fibrillation occurs suddenly, and many times can only be corrected by discharging electrical energy into the atria of the heart of the patient. This treatment is preferably synchronized to a detected R wave of the heart in order to avoid shocking the atria during the T wave or vulnerable period of the heart. The amount of energy which may be required to successfully cardiovert the atria can be as low as one joule and as high as six joules. In most cases, energy of about two to four joules is required to cardiovert atrial fibrillation back to normal sinus rhythm (NSR).

Atrial flutter is a less common accelerated atrial arrhythmia. It is a more organized arrhythmia than atrial fibrillation characterized by a very fast and substantially constant atrial rate. The ventricles of the heart are not able to beat at the atrial rate and generally beat only once for each group of a number of atrial beats. The ratio of atrial beats to ventricular beats is believed to be controlled by the atrioventricular node and may be two or three or more to one and may vary often during an atrial flutter episode.

Atrial flutter results in many of the same symptoms as atrial fibrillation. It can result in dizziness, shortness of breath and a rapid ventricular rate. However, unlike atrial fibrillation, because the ventricular response is generally of a constant rate, the ventricles rarely, if ever, have an opportunity to be fully filled before contracting. As a result, the hemodynamic output of the heart is constantly low and often lower than that experienced during atrial fibrillation.

Atrial flutter is also a relatively stable arrhythmia. It is usually caused by a single re-entrant wavefront in the atria which can become a chronic condition and is characterized by continual circular activation of the atria usually around anatomic obstacles. Atrial flutter episodes, as a result, can last indefinitely unless the re-entrant wavefront is interrupted. Such interruption can be provided by atrial cardioversion.

Implantable atrial defibrillators are known which detect the presence of atrial fibrillation and provide a single cardioverting pulse of electrical energy to the atria when atrial fibrillation is detected. Usually, the therapy is applied in synchronym with a detected R wave to avoid therapy application during the ventricular vulnerable period of the heart thereby preventing the induction of a lethal ventricular arrhythmia. The same therapy has also been suggested for atrial flutter. However, it has been determined that cardioverting atrial flutter synchronized to an R wave requires about the same amount of energy as cardioverting atrial fibrillation synchronized to an R wave. Further, an attempt to cardiovert atrial flutter synchronized to an R wave may even induce atrial fibrillation. This is probably due to the fact that the atrial vulnerable period aligns with the R wave for normally conducted beats. Avoidance of the atrial vulnerable period, by delivering shocks synchronized to atrial activation may allow for lower cardioversion requirements.

Cardioversion synchronized to an A wave, however, must be performed carefully to avoid a cardioversion attempt during the ventricular vulnerable period of the heart. The reason for this is that during atrial flutter, an A wave of the atria can be aligned with or close to a T wave of the ventricle. Hence, an attempt to cardiovert atrial flutter synchronized to any A wave could be potentially problematic with respect to the ventricles.

The present invention enables lower energy cardioversion of atrial flutter. It accomplishes low energy cardioversion of atrial flutter by the application of cardioverting energy to the atria responsive to detection of an A wave and more particularly at a predetermined time after a detected A wave. Safety is assured by defining an inhibit interval responsive to each detected R wave to avoid T waves.

SUMMARY OF THE INVENTION

The invention provides an atrial cardioverter for cardioverting atrial flutter. The atrial cardioverter includes a lead system having a plurality of electrodes to deliver a cardioverting pulse to atria of a heart, for sensing A waves of the heart, and for sensing R waves of the heart. A first detector detects the A waves sensed by the lead system and a second detector detects the R waves sensed by the lead system. An inhibit stage defines an inhibit time period responsive to each detected R wave, and an output provides the cardioverting pulse to the lead system responsive to an A wave being detected, and an inhibit stage precludes provision of the cardioverting pulse during each inhibit time period.

The invention further provides a method of cardioverting atrial flutter including the steps of detecting A waves of a heart, detecting R waves of the heart, defining an inhibit time period responsive to each detected R wave, and providing a cardioverting pulse of electrical energy to the atria of the heart responsive to an A wave being detected, while precluding the provision of the cardioverting pulse of electrical energy during each inhibit time period.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements and wherein:

DETAILED DESCRIPTION OF THE PREFERRED EMBODIMENT

Figure 1:
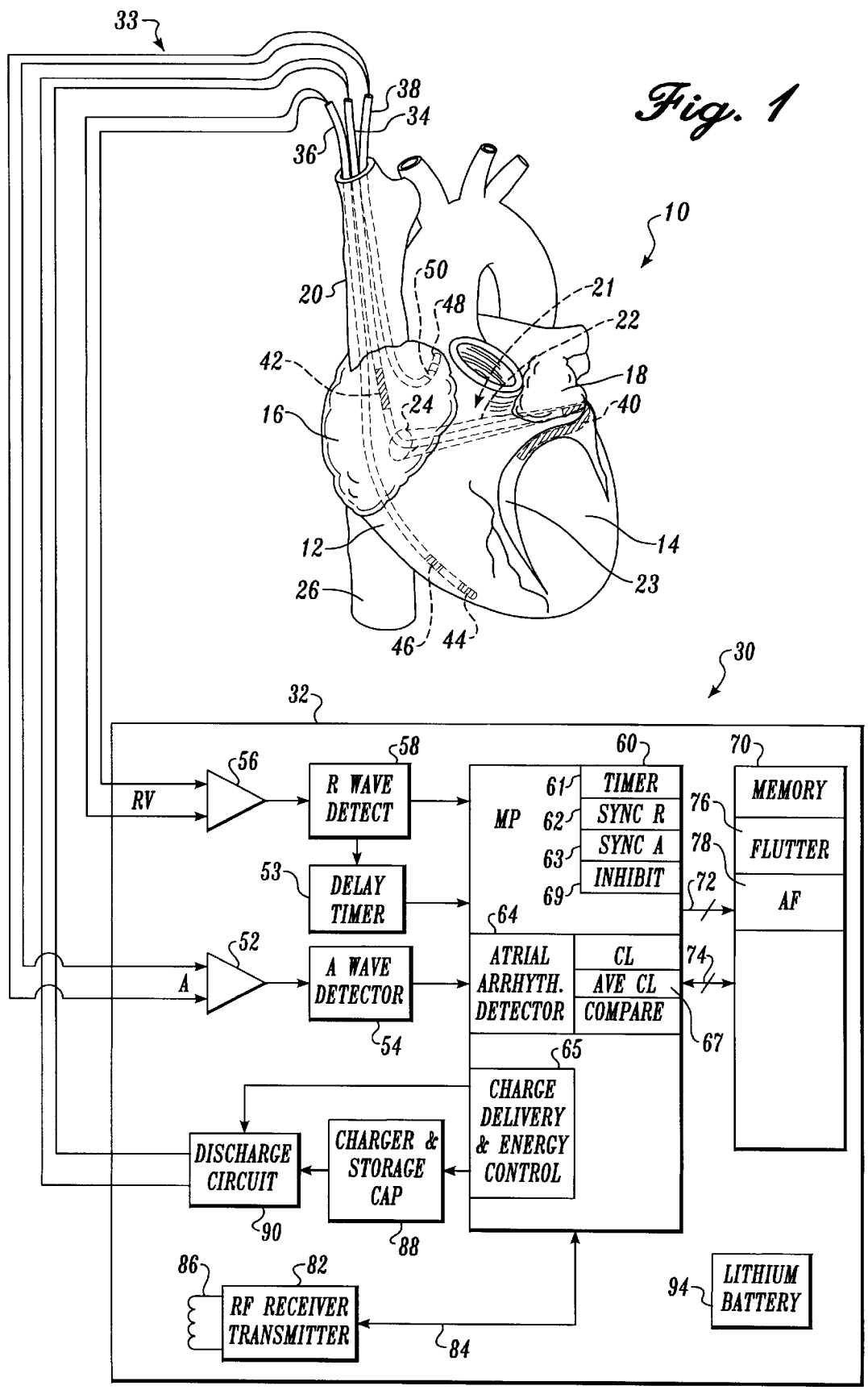
FIG. 1 is a schematic block diagram of a fully implantable atrial cardioverter/defibrillator embodying the present invention, shown in association with a human heart in need of atrial arrhythmia monitoring and potential cardioversion.

Referring now to FIG. 1, it illustrates a fully implantable atrial cardioverter/defibrillator 30 embodying the present invention shown in association with a schematically illustrated human heart 10 in need of atrial arrhythmia monitoring and potential cardioversion. The portions of the heart 10 illustrated in the FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 26.

The atrial cardioverter/defibrillator 30 generally includes an enclosure 32 for hermetically sealing the internal circuit elements of the atrial cardioverter/defibrillator, to be described hereinafter, and a lead system 33 including an intravascular lead 34, a first endocardial lead 36, and a second endocardial lead 38. The enclosure 32 and the leads 34, 36 and 38 are arranged to be implanted beneath the skin of a patient so as to render the atrial cardioverter/defibrillator 30 fully implantable.

The intravascular lead 34 generally includes a first or tip elongated electrode 40, and a second or proximal elongated electrode 42. As illustrated, the lead 34 is flexible and arranged to be passed down the superior vena cava 20, into the right atrium 16, into the coronary sinus ostium 24, and advanced into the coronary sinus channel 21 of the heart near the left side thereof, so that the electrode 40 is within the coronary sinus channel 21 either within the coronary sinus 22 adjacent the left ventricle 14 and beneath the left atrium 18, or most preferably within the great cardiac vein 23 beneath the left atrium 18. The electrodes 40 and 42 are spaced apart such that when the first electrode 40 is positioned as described above, the second electrode 42 is in the right atrium 16. The first electrode 40 together with the second electrode 42 provide for the delivery of cardioverting/defibrillating electrical energy to the atria, in a manner to be described subsequently.

The first endocardial lead 36 preferably includes a bi-polar pair of electrodes 44 and 46, arranged for establishing electrical contact with the right ventricle 12 of the heart 10. The electrodes 44 and 46 permit bi-polar sensing of ventricular activations (R waves) in the right ventricle. As illustrated, the lead 36 is fed through the superior vena cava 20, into the right atrium 16, and then into the right ventricle 22.

The second endocardial lead 38 also preferably includes a bi-polar pair of electrodes 48 and 50, arranged for establishing electrical contact with the right atrium 16 of the heart 10. The electrodes 48 and 50 are closely spaced apart for sensing localized activity of the right atrium. As illustrated, the lead 38 is fed through the superior vena cava 20, into the right atrium 16. The distal end of the lead 38 is substantially "J" shaped in a manner known in the art to position electrodes 48 and 50 in the appendage of the right atrium.

Within the enclosure 32, the atrial cardioverter/defibrillator 30 includes a first sense amplifier 52, an atrial or A wave detector 54, a second sense amplifier 56, and an R wave detector 58. The first sense amplifier 52 forms a first sensing means which, together with the electrodes 48 and 50 of the second endocardial lead 38 to which sense amplifier 52 is coupled, senses localized activity of the right atrium 16 to provide an electrogram signal to the A wave detector 54. The second sense amplifier 56 forms a second sensing means which, together with electrodes 44 and 46 of the first endocardial lead 36 to which it is coupled, senses cardiac activity in the right ventricle of the heart to provide a second electrogram signal to the R wave detector 58.

The R wave detector 58 preferably includes a differentiating filter for differentiating the electrogram signal provided by sense amplifier 56. The R wave detector 58 further preferably includes a threshold circuit for setting an upper and lower threshold to provide an output when the upper or lower threshold is exceeded. The thresholds are set, as known in the art, so that only R waves will have sufficient amplitude to exceed the thresholds of the R wave detector.

The A wave detector 54 similarly preferably includes a differentiating filter for differentiating the first electrogram signal, and a threshold circuit for setting an upper and lower threshold. When the differentiated first electrogram signal transitions beyond either the upper or lower threshold, the atrial event detector 54 provides an output indicating the occurrence of an atrial event.

The enclosure 32 of the atrial cardioverter/defibrillator 30 further includes a microprocessor 60. The microprocessor 60 is preferably implemented in accordance with this embodiment of the present invention to result in a plurality of functional stages. The stages include a timer 61, a first synchronization stage 62, a second synchronization stage 63, and an inhibit stage 69. The stages further include an atrial arrhythmia detector 64 and a charge delivery and energy control stage 65. The atrial arrhythmia detector 64 includes an atrial cycle length determining stage 66, an average cycle length determining stage 67, and a compare stage 68.

The microprocessor 60 is arranged to operate in conjunction with a memory 70 which is coupled to the microprocessor 60 by a multiple-bit address bus 72, and a bi-directional multiple-bit data bus 74. This permits the microprocessor 60 to address desired memory locations within the memory for executing write or read operations. During a write operation, the microprocessor stores data, such as atrial cycle lengths, or operating parameters, such as atrial arrhythmia type classifying criteria, in the memory at the addresses defined by multiple-bit addresses conveyed over the address bus 72, and conveys the operating parameters and data to the memory 70 over the multiple-bit data bus 74. During a read operation, the microprocessor 60 obtains data or operating parameters from the memory at the storage locations identified by the multiple-bit addresses provided over the address bus 72 and receives the operating parameters and data from the memory over the bi-directional data bus 74.

For entering programmable operating parameters into the memory 70, as for example, cardioverting or defibrillating peak voltages, or further, for example, atrial arrhythmia detection criteria into memory portions 76 and 78, the microprocessor 60 receives the programmable operating parameters from an external controller (not shown) which is external to the skin of the patient. The external controller may be arranged to communicate with a receiver/transmitter 82 within enclosure 32 which is coupled to the microprocessor 60 over a bi-directional bus 84. The receiver/transmitter 82 receives the programmable parameters from the external controller and then conveys the same to the microprocessor 60 for storage in memory 70. The receiver/transmitter 82 also conveys various information which it obtains from the microprocessor over bus 84 to the external controller.

The receiver/transmitter 82 includes a transmitting coil 86 so that the receiver/transmitter 82 and coil 86, together with the external controller, form a communication system. Such communication systems are well known in the art. One preferred communication system is disclosed in U.S. Pat. No. 5,342,408, which issued on Aug. 30, 1994, for "TELEMETRY SYSTEM FOR AN IMPLANTABLE CARDIAC DEVICE," which patent is assigned to the assignee of the present invention and incorporated herein by reference.

To complete the identification of the various structural elements within the enclosure 32, the atrial cardioverter/defibrillator 30 further includes a charger and storage capacitor circuit 88 of the type well known in the art which charges a storage capacitor to a selected peak voltage, and a discharge circuit 90 for discharging the storage capacitor within circuit 88 for a predetermined time to provide a controlled discharge output of electrical energy to the atria of the heart when required. To that end, the discharge circuit 90 is coupled to electrodes 40 and 42 of the intravascular lead 34 for applying the cardioverting or defibrillating electrical energy to the atria. Lastly, the cardioverter/defibrillator 30 includes a depletable power source 94, such as a lithium battery, for providing power to the electrical components of the atrial cardioverter/defibrillator 30.

Atrial arrhythmia detection criteria are established in the memory 70 and more particularly in memory portions 76 and 78. Memory portion 76 stores criteria for atrial flutter and memory portion 78 stores criteria corresponding to atrial fibrillation.

At predetermined times the atrial arrhythmia detector 64 is activated to determine if an atrial arrhythmic episode is occurring in the atria, and to classify the arrhythmia if one is present. The atrial cycle length determining stage 66 determines, over a predetermined time or over a predetermined number of atrial cardiac cycles, the atrial cardiac cycle lengths of the heart, and stores the cycle lengths in memory 70. The atrial cardiac cycle lengths are the time spans between adjacent atrial events as identified by the A wave detector 54. Once the cycle lengths are determined, an average cycle length is determined by the average cycle length determining stage 67. The average cycle length is then compared by the compare stage 68 to the atrial arrhythmia type classification criteria stored in memory portions 76 and 78.

First, the microprocessor 60 accesses normal sinus rhythm criteria stored in memory 70 to determine if the atria are in normal sinus rhythm. More specifically, if the average cycle length is greater than a stored criteria of 250 milliseconds, for example, the atria are considered to be in normal sinus rhythm and, hence, an absence of atrial arrhythmia is considered to have been detected. If the atria are not in normal sinus rhythm and, hence, experiencing an arrhythmic episode, the type of atrial arrhythmia is then determined.

To determine whether the atria are in flutter or fibrillation, the microprocessor 60 first accesses the memory portion 76 which establishes atrial flutter criteria. If the average atrial cardiac cycle length is less than 250 milliseconds, but greater than the 150 millisecond criteria stored in memory portion 76, the atria are considered to be in atrial flutter. A therapy in accordance with the present invention, is then applied to the atria.

If the atria are not in atrial flutter, the microprocessor 60 then accesses the memory portion 78 which establishes a criteria for atrial fibrillation. If the compare stage 68 determines that the average atrial cardiac cycle length is less than 150 milliseconds, the atria are considered to be in atrial fibrillation. An atrial fibrillation therapy is then applied to the atria. In accordance with this preferred embodiment, the therapy applied to the atria to cardiovert or defibrillate the atrial fibrillation is electrical atrial cardioversion or defibrillation having an energy in the range of between 1 joule and 6 joules. To apply this therapy, the capacitor of circuit 88 is charged to a preprogrammed voltage. The synchronization stage 62 then analyzes ventricular activity in a manner known in the art to identify a safe R wave for synchronizing the applied energy. When such an R wave is located, the synchronization stage 62 causes the charge delivery and energy control 65 to activate the discharge circuit 90 which in turn discharges the capacitor. The discharged voltage is provided to electrodes 40 and 42 for applying the same to the atria 16 and 18.

Figure 2:
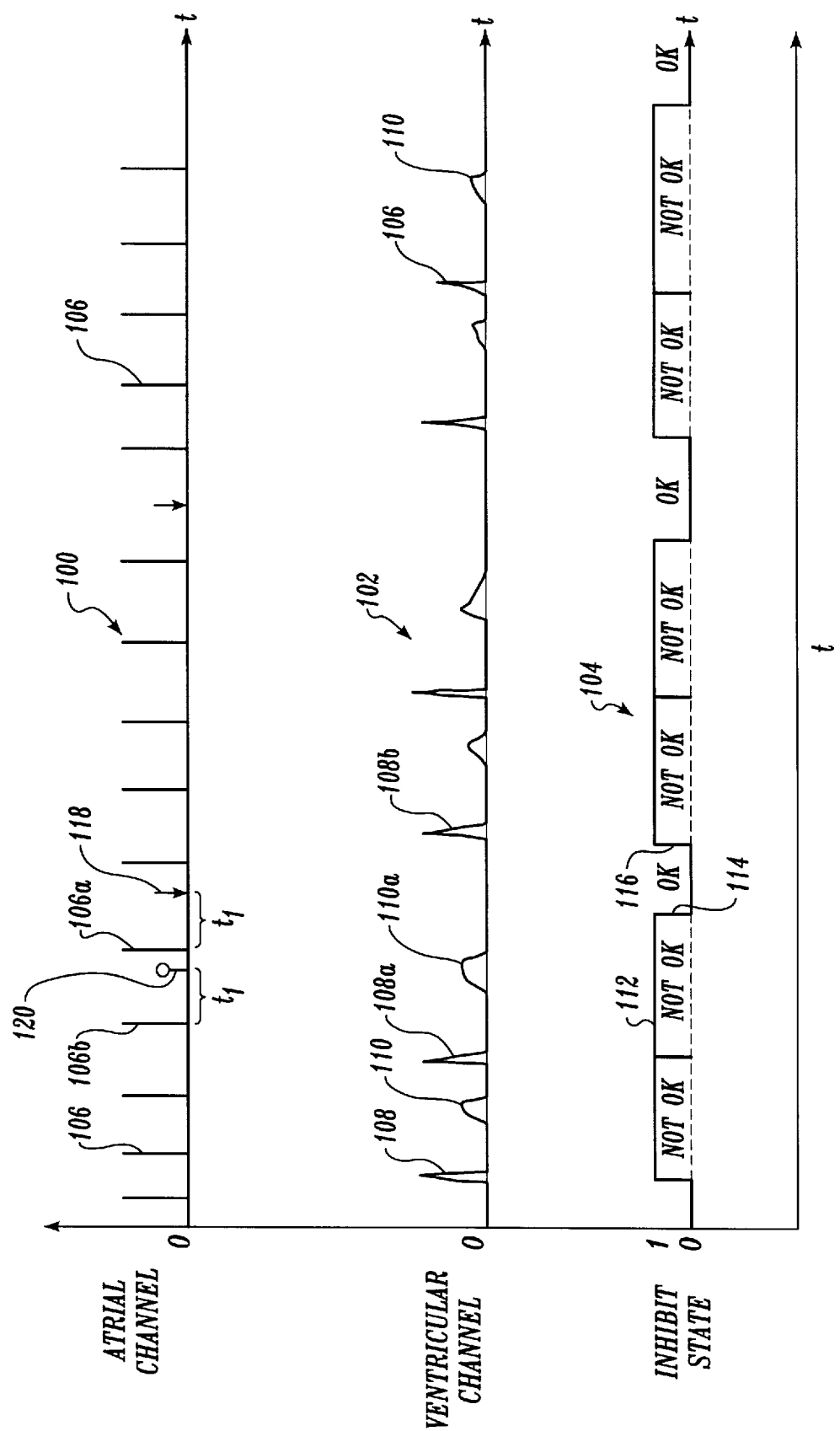
FIG. 2 is a plot of three simultaneous waveforms as a function of time illustrating the operation of the present invention in accordance with one preferred embodiment thereof.

Referring now to FIG. 2, the atrial flutter therapy in accordance with one embodiment of the present invention will now be described. FIG. 2 illustrates three different, time aligned, waveforms. The first waveform 100 illustrates the output of the A wave detector 54 versus time. The second waveform 102 illustrates the output of sense amplifier 56 so that both R waves and T waves may be illustrated. Lastly, the third waveform 104 is that of the state of the inhibit stage 69.

As previously mentioned, atrial flutter is an accelerated atrial arrhythmia characterized by a high and substantially constant atrial rate and a rapid and at times varying ventricular rate. Ventricular activations or R waves are followed by repolarizations or T waves which must be avoided since shocking the heart on or near a T wave could accelerate the heart into ventricular fibrillation. Waveform 100 illustrates the detection of A waves 106 occurring at a much faster rate than the R waves 108 of waveform 102. In waveform 102, the T waves 110 may also be noted.

In accordance with the present invention, it has been discovered that during atrial flutter, there is at least one recurring point in time between successive A waves where the threshold energy for successfully cardioverting flutter is a minimum. Hence, in accordance with the present invention, to cardiovert atrial flutter, the cardioverting electrical energy is applied in response to detection of an A wave, and more particularly, at a predetermined time after an A wave is detected and which is not within the vulnerable period or region of the ventricles. In doing so, the electrical energy is safely applied without inducing life threatening ventricular fibrillation. The patient is shocked with the least amount of energy possible which will also successfully cardiovert the flutter. Hence the patient experiences little if any discomfort during the process. Lastly, battery power is conserved thus extending the useful life of the implanted device.

In accordance with the present invention, an unsafe time to apply the shock is determined from the ventricular sense channel including lead 36 with electrodes 44 and 46, sense amplifier 56, and R wave detector 58. This is preferably accomplished by the inhibit stage 69. Responsive to the detection of each R wave, the inhibit stage 69 which preferably comprises a timer, times a preset and fixed inhibit time period or interval having a duration long enough to allow each T wave to occur and fully dissipate. Inhibit intervals between 250 and 600 milliseconds may be employed in practice. As long as the inhibit stage is counting time, the inhibit state is a logical 1, for example, and will preclude delivery of the cardioverting energy.

As an example of the above, it will be noted that upon the detection of R wave 108a, the inhibit stage 69 is reset and begins timing. While it times the inhibit time interval, its state is a logical 1 as indicated at 112. When the inhibit time interval timing is completed at 114, it is now safe to apply the cardioverting energy until the next R wave 108b is detected at which time the inhibit timer resets and begins to time another inhibit time interval starting at 116. It may be noted that the inhibit time interval ending at 114 ended after the T wave 110a of R wave 108a had terminated. As a result, it is assured that the cardioverting energy is not applied during the T wave vulnerable period of the heart.

As previously mentioned, the cardioverting energy is applied responsive to the detection of an A wave by the A wave detector 54. More specifically, the cardioverting energy is applied a predetermined time interval after an A wave is detected in order to cardiovert at the minimum threshold, so long as it is not inhibited by the inhibit stage 69. For example, A wave detection 106a may be used to effect cardioversion. If the predetermined time interval after A wave detection to apply the cardioverting energy is $t_1$, then at time 118, the cardioverting energy may be applied if it is not inhibited. As can be noted in FIG. 2, time 118 occurs after time 114 and before time 116. Hence, it will not be inhibited and the cardioverting energy to cardiovert atrial flutter may be applied at time 118 responsive to the A wave detection 106a. Cardioverting energies in the range of 50 to 500 millijoules may be used in practice. Conventional cardioverting pulse durations between six and twenty milliseconds are appropriate in practicing the present invention.

The predetermined time interval ($t_1$) is preferably timed by the atrial synchronizing stage 63 which preferably comprises a timer. After atrial flutter is detected, each A wave detected by A wave detector 54 causes the atrial synchronizing stage 63 to time the predetermined time.

The predetermined time interval ($t_1$) is preferably a programmable parameter. It may be determined at implant through testing. It may further be determined over time by noting successful flutter cardioversion energies and the time relations to their immediately preceding A wave detections at which they were applied.

As an example of cardioverting energy application inhibition, it may be noted that A wave detection 106b results in a potential application of cardioverting energy at time 120. However, at time 120, the inhibit state is a logical 1 and hence therapy application at time 120 will be inhibited.

In accordance with a further embodiment, the inhibit time interval for each detected R wave may be shortened to afford more opportunity for therapy application. Within approximately the first fifty milliseconds following an R wave, the ventricles are refractory and will not respond adversely to an applied shock. As a result, the commencement of timing the inhibit time interval may be delayed by a predetermined time, such as fifty milliseconds. The delay in timing commencement may be accomplished with a delay timer 53 capable of triggering the inhibit timer a predetermined delay time after each R wave is detected by R wave detector 58.

While in accordance with this preferred embodiment the discrimination between atrial fibrillation and atrial flutter is determined by atrial cardiac cycle length alone, atrial cardiac cycle length variability may also be used in combination therewith for discrimination purposes. If such variability is employed, the compare stage 68 may compare each determined atrial cardiac cycle length to the average cycle length. The maximum difference therebetween may then be used as a discriminating factor. Atrial flutter and atrial fibrillation may also be determined through the use of correlation functions applied, for example, to the atrial activity sensed at different areas of the atria. Such correlation functions are well known in the art.

In addition, although real time processing of the atrial activity to determine the atrial cardiac cycle lengths is contemplated by this preferred embodiment, it will be appreciated by those skilled in the art that such determinations may be made from data stored in memory during a data acquisition period prior to the atrial arrhythmia detector being activated for operating on the stored data to determine the atrial cardiac cycle lengths, the average cycle length, and the maximum variance between the cycle lengths and the average cycle length. Hence, while a particular embodiment of the present invention has been shown and described, modifications may be made and it is therefore intended in the appended claims to cover all such changes and modifications which fall within the true spirit and scope of the invention.

What is claimed is:

1. An atrial cardioverter for cardioverting atrial flutter comprising:

a lead system having a plurality of electrodes to deliver a cardioverting pulse to atria of a heart, for sensing A waves of the heart, and for sensing R waves of the heart;

an atrial flutter detector;

a first detector for detecting the A waves sensed by the lead system;

a second detector for detecting the R waves sensed by the lead system;

inhibit means for defining an inhibit time period responsive to each detected R wave; and output means for providing the cardioverting pulse to the lead system when the heart is in atrial flutter and responsive to an A wave being detected, said inhibit means precluding provision of the cardioverting pulse during each inhibit time period.

2. An atrial cardioverter as defined in claim 1 wherein the inhibit means includes a timer for timing the inhibit time period.

3. An atrial cardioverter as defined in claim 1 wherein the inhibit means includes a timer for timing the inhibit time period commencing with the detection of each R wave.

4. An atrial cardioverter as defined in claim 1 wherein the inhibit means includes a timer for timing the inhibit time period commencing a predetermined time after the detection of each R wave.

5. An atrial cardioverter as defined in claim 1 further including a timer for causing the output means to provide the cardioverting pulse to the lead system a predetermined time after detection of an A wave.

6. A method of cardioverting atrial flutter including the steps of:

detecting atrial flutter;

detecting A waves of a heart;

detecting R waves of the heart;

defining an inhibit time period responsive to each detected R wave; and providing a cardioverting pulse of electrical energy to the atria of the heart responsive to an A wave being detected, and precluding the provision of the cardioverting pulse of electrical energy during each inhibit time period.

7. A method as defined in claim 6 wherein the inhibit period defining step includes timing an inhibit time period responsive to detecting each R wave.

8. A method as defined in claim 7 wherein the inhibit period defining step further includes commencing the timing of the inhibit time period with the detection of each R wave.

9. A method as defined in claim 7 wherein the inhibit period defining step includes commencing the timing of the inhibit time period a predetermined time after the detection of each R wave.

10. A method as defined in claim 6 wherein the providing step further includes providing the cardioverting pulse a predetermined time after detection of an A wave.

11. An atrial cardioverter for cardioverting atrial flutter comprising:

a lead system having a plurality of electrodes to deliver a cardioverting pulse to atria of a heart, for sensing A waves of the heart, and for sensing R waves of the heart;

an atrial flutter detector;

a first detector for detecting the A waves sensed by the lead system;

a second detector for detecting the R waves sensed by the lead system;

inhibit means for defining an inhibit time period responsive to each detected R wave; and output means for providing a single cardioverting pulse to the lead system when the heart is in atrial flutter and responsive to an A wave being detected, said inhibit means precluding provision of the cardioverting pulse during each inhibit time period.

12. A method of cardioverting atrial flutter including the steps of:

detecting atrial flutter;

detecting A waves of a heart;

detecting R waves of the heart;

defining an inhibit time period responsive to each detected R wave; and providing a single cardioverting pulse of electrical energy to the atria of the heart responsive to an A wave being detected, and precluding the provision of the cardioverting pulse of electrical energy during each inhibit time period.

* * * * *